(12) United States Patent
Guo et al.

(10) Patent No.: US 6,217,895 B1
(45) Date of Patent: Apr. 17, 2001

(54) METHOD FOR TREATING AND/OR PREVENTING RETINAL DISEASES WITH SUSTAINED RELEASE CORTICOSTEROIDS

(75) Inventors: Hong Guo, Belmont; Paul Ashton, Boston, both of MA (US)

(73) Assignee: Control Delivery Systems, Watertown, MA (US)

( * ) Notice: Subject to any disclaimer, the term of this patent is extended or adjusted under 35 U.S.C. 154(b) by 0 days.

(21) Appl. No.: 09/273,548

(22) Filed: Mar. 22, 1999

(51) Int. Cl.$^7$ .................................................. A61F 2/00
(52) U.S. Cl. ................................................ 424/427
(58) Field of Search ..................... 424/427, 428

(56) References Cited

U.S. PATENT DOCUMENTS

| | | |
|---|---|---|
| 5,378,475 | 1/1995 | Smith et al. . |
| 5,773,019 | 6/1998 | Ashton et al. . |
| 5,902,598 | 5/1999 | Chen et al. . |

OTHER PUBLICATIONS

J.K. Challa et al., "Exudative Macular Degeneration and Intravitreal Triamicinolone: 18 Month Follow Up," *Australian and New Zealand Journal of Ophthalmology*, Nov. 1998vol. 26 (4), pp. 277–281.

G. J. Jaffe et al., "Safety, Efficacy, and Pharmacokinetics of an Intravitreal, Fluocinolone Sustained Drug Delivery System," *Investigative Ophthalmology & Visual Science*, Mar. 15, 1999, vol. 40 (4), (APVO Abstract Book), pp. S988.

P. A. Pearson et al., "Clearance and Distribution of Ciprofloxacin After Intravitreal Injection," *Retina*, 1993, vol. 13(4), pp. 326–330.

P. A. Pearson et al., "Evaluation of a Delivery System Providing Long–term Release of Cyclosporine," *Arch Ophthalmol.*, 1996, vol. 114, pp. 311–317.

R. Perasalo, "The Prevalence of Macular Degeneration in a Cohort of Institutionalized Geriatric Glaucoma Patients," *Acta Ophthalmol*, Apr. 1994, vol. 72(2), pp. 175–177.

*Primary Examiner*—Carlos A. Azpuru
(74) *Attorney, Agent, or Firm*—McDermott, Will & Emery

(57) ABSTRACT

The present invention relates to a method for administering a corticosteroid to a posterior segment of an eye. In the method, a sustained release device is implanted to deliver the corticosteroid to the eye. The aqueous corticosteroid concentration remains less than vitreous corticosteroid concentration during release of the corticosteroid from the device.

21 Claims, 2 Drawing Sheets

METHOD FOR TREATING AND/OR PREVENTING RETINAL DISEASES WITH SUSTAINED RELEASE CORTICOSTEROIDS

FIELD OF THE INVENTION

The present invention relates to the field of controlled pharmaceutical delivery, particularly to corticosteroids.

BACKGROUND OF THE INVENTION

Compounds classified as corticosteroids, such as triamcinolone, can effectively treat some forms of neovascularization such as corneal neovasularization. In general, corticosteroids have been unsuccessful in treating neovscularization of the posterior segment. In many patients, these compounds cause undesirable side effects. These adverse affects include elevations in intraocular pressure and the formation of, or acceleration of, the development of cataracts. Elevations in intraocular pressure are of particular concern in patients who are already suffering from elevated intraocular pressure, such as glaucoma patients. Moreover, a risk exists that the use of corticosteroids in patients with normal intraocular pressure will cause elevations in pressure that result in damage to ocular tissue. Since therapy with corticosteroids is frequently long term, i.e., several days or more, a potential exists for significant damage to ocular tissue as a result of prolonged elevations in intraocular pressure attributable to that therapy.

One approach to solving the foregoing problems has been to search for specific compounds which are effective in treating neovascularization without elevating intraocular pressure. Another approach has been to administer corticosteroids in conjunction with another drug to "block" or reduce the IOP elevating effects of the corticosteroids or to treat IOP elevation separately with another drug. A further approach has been to intravitreally inject corticosteroids to treat ocular neovascularization.

There exists a need for an improved method for treating and/or preventing retinal diseases with corticosteroids.

DISCLOSURE OF THE INVENTION

An object of the present invention is to provide a method for treating and/or preventing ocular diseases which have neovascularization as a component with corticosteroids without the associated adverse side effects.

Additional objects, advantages and other features of the invention will be set forth in the description which follows and in part will become apparent to those having ordinary skill in the art upon examination of the following or may be learned from the practice of the invention. The objects and advantages of the invention may be realized and obtained as particularly pointed out in the appended claims.

According to the present invention, the foregoing and other objects are achieved in part by a method for administering a corticosteroid to a posterior segment of an eye, the method comprising the step of:

implanting a sustained release device to deliver the corticosteroid to the vitreous of the eye wherein aqueous corticosteroid concentration is less than vitreous corticosteroid concentration during release.

In accordance with the present invention, the foregoing and other advantages are also achieved in part by an implantable, sustained release device for administering a corticosteroid to a posterior segment of an eye, the device comprising:

a corticosteroid, wherein the device is configured to provide sustained release of the corticosteroid to the vitreous of the eye such that aqueous corticosteroid concentration remains less than vitreous corticosteroid concentration during the release.

Additional objects and advantages of the present invention will become readily apparent to those skilled in this art from the following detailed description, wherein embodiments of the invention are described simply by way of illustrating of the best mode contemplated in carrying out the invention. As will be realized, the invention is capable of other and different embodiments, and its several details are capable of modifications in various obvious respects, all without departing from the invention. Accordingly, the drawings and description are to be regarded as illustrative in nature and not as restrictive.

DESCRIPTION OF THE INVENTION

Figure 1:
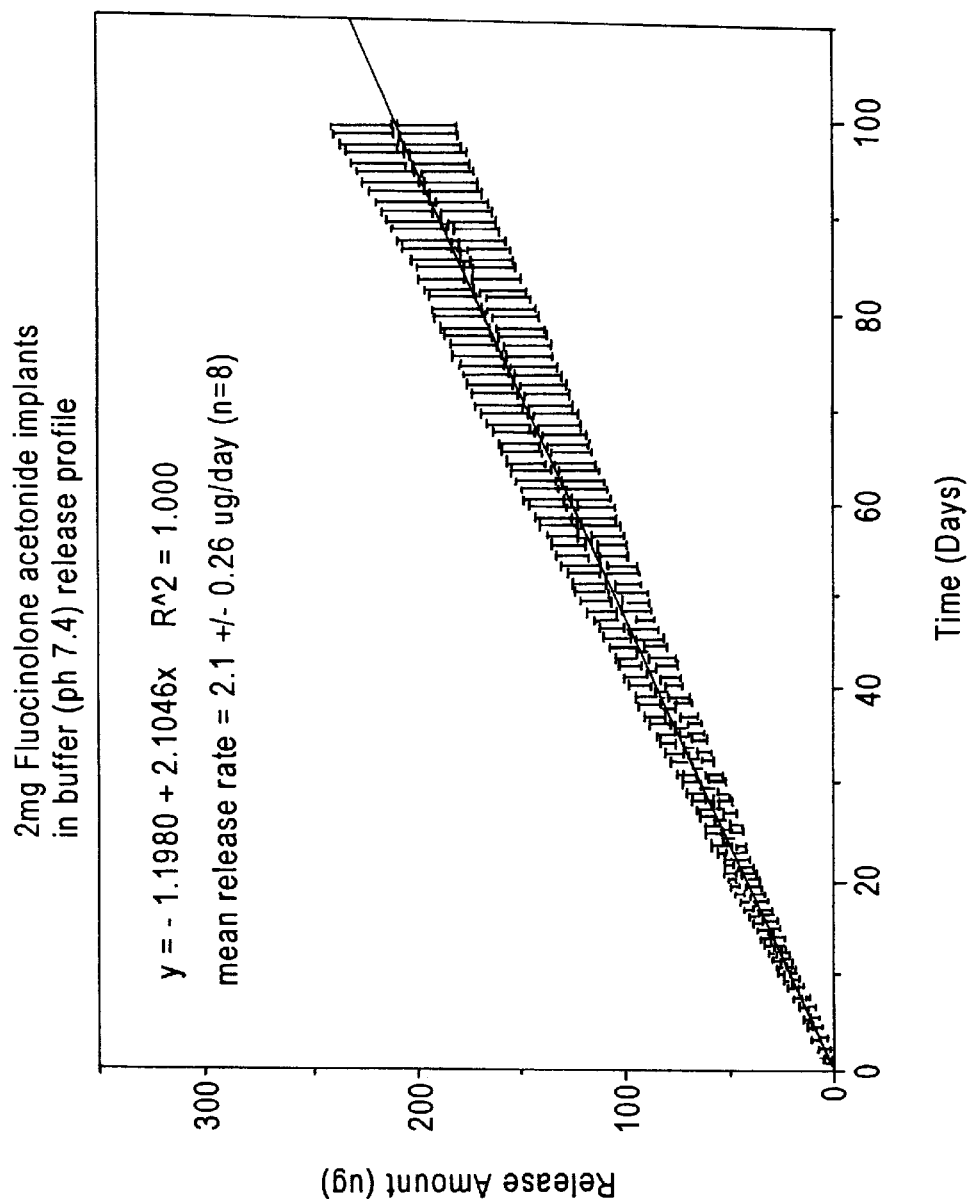
FIG. 1 shows the sustained release profile of a 2 mg fluocinolone acetonide implant in buffer.

The present invention provides a method for delivering a therapeutic amount of a corticosteroid to the vitreous of an eye but prevents toxic amounts of the corticosteroid from accumulating in the aqueous. The method comprises the step of implanting a sustained release device comprising a corticosteroid to the posterior segment to deliver the corticosteroid to the vitreous wherein aqueous corticosteroid concentration is less than vitreous corticosteroid concentration during release of the corticosteroid.

The present invention is particularly effective in treating diseases of the retina, retinal pigment epithelium (RPE) and choroid. These diseases include, for example, ocular neovascularization, ocular inflammation and retinal degenerations. Specific examples of these disease states include diabetic retinopathy, chronic glaucoma, retinal detachment, sickle cell retinopathy, senile macular degeneration, retinal neovascularization, subretinal neovascularization; rubeosis iritis inflammatory diseases, chronic posterior and pan uveitis, neoplasms, retinoblastoma, pseudoglioma, neovascular glaucoma; neovascularization resulting following a combined vitrectomy and lensectomy, vascular diseases retinal ischemia, choroidal vascular insufficiency, choroidal thrombosis, neovascularization of the optic nerve, diabetic macular edema, cystoid macular edema, macular edema, retinitis pigmentosa, retinal vein occlusion, proliferative vitreoretinopathy, angioid streak, and retinal artery occlusion, and, neovascularization due to penetration of the eye or ocular injury.

Examples of corticosteroids useful in the present invention include, for example, triamcinolone, dexamethasone, fluocinolone, cortisone, prednisolone, flumetholone, and derivatives thereof.

By "sustained release device" it is meant a device that releases drug over an extended period of time in a controlled fashion. Examples of sustained release devices useful in the present invention may be found in, for example, U.S. Pat. No. 5,378,475 and U.S. Pat. No. 5,773,019, and U.S. Ser. No. 08/919,221 filed on Aug. 28, 1997.

By "vitreous" of the eye, it is meant the vitreous or vitreal cavity of the eye. By "aqueous" of the eye, it is meant the aqueous humor of the eye.

In the present invention, a sustained release device is implanted into the eye such that it delivers corticosteroid to the posterior segment of the eye. In a preferred embodiment, the sustained release device is implanted intravitreally. However, the device may also be implanted in the choroidal space, sub-retinally, or in the sclera. These methods of administration and techniques for their preparation are well known by those of ordinary skill in the art. Methods of administration and techniques for their preparation are set forth in Remington's Pharmaceutical Sciences.

The aqueous corticosteroid concentration remains less than the vitreous corticosteroid concentration for substantially the lifetime of the sustained release device. Thus, during release of the corticosteroid, the aqueous corticosteroid concentration is about 0.002 µg/ml to about 0.01 µg/ml, such as from about 0.01 µg/ml to about 0.05 µg/ml. Preferably, the aqueous corticosteroid concentration is less than about 0.05 µg/ml.

Is contrast, during release of the corticosteroid, the vitreous corticosteroid concentration remains therapeutic, that is, less than about 10 µg/ml. The exact desired concentration depends upon the disease and therapeutic index of the drug.

The sustained release device useful in the present invention is any device which can be implanted to deliver corticosteroid to the vitreous of the eye and can release a corticosteroid for a sustained period of time, that is, for about 1 month to about 20 years, such as from about 6 months to about 5 years.

The sustained release device can be prepared to release the corticosteroid by pseudo zero order kinetics with a mean release rate of about 1 µg/day to about 50 µg/day, such as, about 1 µg/day to about 10 µg/day.

The following non-limiting examples are given by way of illustration only.

EXAMPLE 1

Sustained release fluocinolone acetonide devices were implanted into the vitreous of 4 rabbits while animals in the control group received a sham operation. After implantation, all rabbits received a sub-retinal injection of gelatin microspheres releasing basic fibroblast growth factor. All control animals developed neovascularization while ¾ of the implant group showed no evidence of neovascularization. No animals showed any indication of ocular or systemic steroid-induced toxicity.

EXAMPLE 2

Animals received intravitreal fluocinolone acetonide implants and were sacrificed at 1 month, 4 months, and 11 months. Samples of the vitreous and aqueous were collected for analysis by HPLC. Analysis was performed using a fully automated Hitachi HPLC system. The mobile phase was 40% acetonitrile buffered to a pH of 4.0. The flow rate was 1.0 ml/min with an Axxion C-18 column (25 cm×4 mm×5 µm) and UV detection at 238 nm. Intravitreal levels were found to be relatively constant throughout the study (0.1–0.2 µg/ml) while no steroid was detected in the aqueous humor (limit of detection 0.02 µg/ml).

DETAILED DESCRIPTION OF THE DRAWINGS

FIG. 1 shows the sustained release profile of a 2 mg flucinolone acetonide implant in buffer over 100 days. The mean release rate was 2.1+/−0.26 µg/day.

Figure 2:
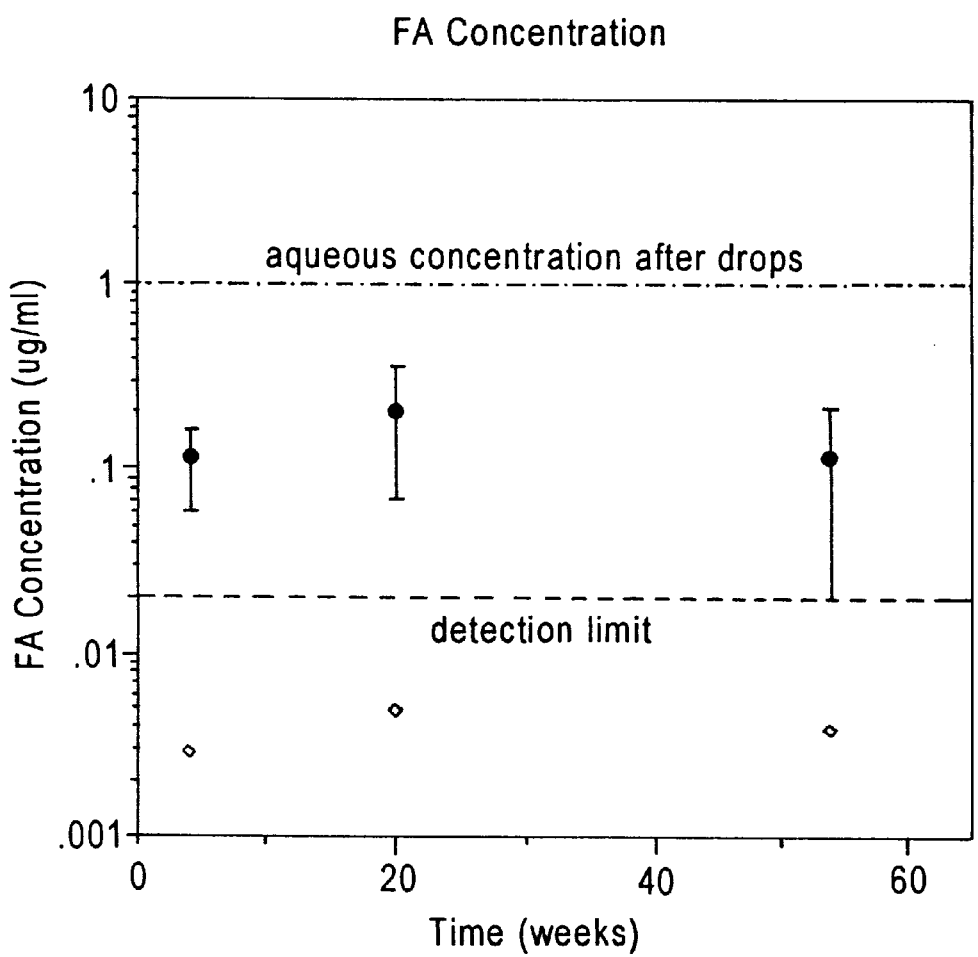
FIG. 2. shows the vitreous and aqueous levels of fluocinolone acetonide after implantation of a sustained release device.

FIG. 2 shows the vitreous and aqueous levels of fluocinolone acetonide after implantation of a sustained release device. Animals were sacrificed at 4 weeks, 20 weeks, and 1 year. FIG. 2 shows that therapeutic levels are maintained in the vitreous while drug levels in the aqueous humor were below the detection limit of the assay.

In the previous descriptions, numerous specific details are set forth, such as specific materials, structures, chemicals, processes, etc., in order to provide a better understanding of the present invention. However, the present invention can be practiced without resorting to the details specifically set forth. In other instances, well-known processing structures have not been described in detail in order not to unnecessarily obscure the present invention.

Only the preferred embodiment of the invention and but a few examples of its versatility are shown and described in the present disclosure. It is to be understood that the present invention is capable of use in various other combinations and environments and is capable of changes or modifications within the scope of the inventive concept as expressed herein. All patents, patent applications and publication cited herein are incorporated by reference in their entirety.

What is claimed is:

1. A method for administering a corticosteroid to a posterior segment of an eye, the method comprising the step of:
   implanting a sustained release device to deliver the corticosteroid to the vitreous of the eye and wherein aqueous corticosteroid concentration is less than vitreous corticosteroid concentration during release.

2. A method according to claim 1, wherein aqueous corticosteroid concentration is about 0.002 µg/ml to about 0.01 µg/ml.

3. A method according to claim 2, wherein aqueous corticosteroid concentration is about 0.01 µg/ml to about 0.05 µg/ml.

4. A method according to claim 1, wherein aqueous corticosteroid concentration is non-toxic and is less than 0.05 µg/ml.

5. A method according to claim 1, wherein the device releases corticosteroid for about 1 month to about 20 years.

6. A method according to claim 5, wherein the device releases corticosteroid for about 6 months to about 5 years.

7. A method according to claim 1, wherein the vitreous corticosteroid concentration is therapeutic.

8. A method according to claim 1, wherein the vitreous corticosteroid concentration is less than about 10 µg/ml.

9. A method according to claim 1, wherein the corticosteroid is selected from the group consisting of triamcinolone, dexamethasone, fluocinolone, cortisone, prednisolone, flumetholone, and derivatives thereof.

10. A method according to claim 1, comprising intravitreally implanting the sustained release device.

11. A method according to claim 1, wherein a disease state to be treated is selected from the group consisting of ocular neovascularization, ocular inflammation and retinal degeneration.

12. A method according to claim 1, wherein the sustained release device releases the corticosteroid with pseudo zero order kinetics.

13. A method according to claim 1, wherein the sustained release device has a mean release rate of about 1 µg/day to about 50 µg/day of corticosteroid.

14. A method according to claim 13, wherein sustained release device has a mean release rate of about 1 µg/day to about 10 µg/day of corticosteroid.

15. A method according to claim 1, wherein the sustained release device releases only one drug.

16. An implantable, sustained release device for administering a corticosteroid to a posterior segment of an eye, the device comprising:
   a corticosteroid, wherein the device is configured to provide sustained release of the corticosteroid to the vitreous of the eye such that aqueous corticosteroid concentration remains less than vitreous corticosteroid concentration during the release.

17. A device according to claim 16, wherein the device is configured to provide sustained release of the corticosteroid to the vitreous of the eye such that aqueous corticosteroid concentration remains less than vitreous corticosteroid concentration during the release.

18. A device according to claim 16, wherein the corticosteroid is selected from the group consisting of triamcinolone, dexamethasone, fluocinolone, cortisone, prednisolone, flumetholone, and derivatives thereof.

19. A device according to claim 16, wherein the sustained release device releases the corticosteroid with pseudo zero order kinetics.

20. A device according to claim 16, wherein the sustained release device has a mean release rate of about 1 µg/day to about 50 µg/day of corticosteroid.

21. A device according to claim 16, wherein the sustained release device releases only one drug.

* * * * *